(12) United States Patent
Simpson et al.

(10) Patent No.: US 7,060,060 B1
(45) Date of Patent: Jun. 13, 2006

(54) DIALYSIS PROCEDURE CATHETER

(76) Inventors: Vicki J. Simpson, 6940 Royal Hunt Ridge Dr., Riverside, CA (US) 92506; James D. Simpson, 6940 Royal Hunt Ridge Dr., Riverside, CA (US) 92506

( * ) Notice: Subject to any disclaimer, the term of this patent is extended or adjusted under 35 U.S.C. 154(b) by 113 days.

(21) Appl. No.: 10/839,272

(22) Filed: May 6, 2004

(51) Int. Cl.
*A61M 25/16* (2006.01)

(52) U.S. Cl. .................. 604/537; 604/250; 604/177

(58) Field of Classification Search .............. 606/167; 604/523, 27, 30, 44, 48, 164.01, 164.02, 604/167.01, 167.02, 167.05, 537, 250, 177, 604/167.03, 28, 29, 41, 93.01, 99.01–99.04, 604/165.01–165.03, 181, 186, 187, 246, 604/256, 178, 245, 158, 506, 507, 508, 33, 604/249

See application file for complete search history.

(56) References Cited

U.S. PATENT DOCUMENTS

| | | | | |
|---|---|---|---|---|
| 4,233,975 A | * | 11/1980 | Yerman | 604/110 |
| 4,848,344 A | * | 7/1989 | Sos et al. | 606/194 |
| 5,167,635 A | * | 12/1992 | Haber et al. | 604/164.08 |
| 5,376,075 A | * | 12/1994 | Haughton et al. | 604/158 |
| 5,395,330 A | * | 3/1995 | Marcadis et al. | 604/102.02 |
| 5,697,914 A | * | 12/1997 | Brimhall | 604/177 |
| 5,743,891 A | * | 4/1998 | Tolkoff et al. | 604/526 |
| 6,179,828 B1 | * | 1/2001 | Mottola et al. | 604/523 |
| 6,254,574 B1 | * | 7/2001 | Burzynski et al. | 604/170.01 |
| 6,475,189 B1 | * | 11/2002 | Lilley, Jr. | 604/164.01 |
| 6,629,956 B1 | * | 10/2003 | Polidoro et al. | 604/164.01 |
| 6,638,252 B1 | * | 10/2003 | Moulton et al. | 604/164.01 |

* cited by examiner

*Primary Examiner*—Nicholas Lucchesi
*Assistant Examiner*—Theodore J. Stigell

(57) ABSTRACT

A dialysis procedure catheter for accurately facilitating insertion of a needle into a dialysis patient's body. The dialysis procedure catheter includes a tubular member having a bore being disposed therethrough, and also having an enlarged main portion and a branch portion, and further having a needle; and also includes a plug assembly including a plug member being removably disposed in the bore of the needle; and further includes a handle being attached to the enlarged main portion of the tubular member; and also includes a hose having a first end being attached to the branch portion; and further includes a hose clamp for crimping the hose; and also includes a hose connector being attached to a second end of the hose for connecting to a dialysis machine.

5 Claims, 3 Drawing Sheets

DIALYSIS PROCEDURE CATHETER

BACKGROUND OF THE INVENTION

1. Field of the Invention

The present invention relates to dialysis catheters and more particularly pertains to a new dialysis procedure catheter for accurately facilitating insertion of a needle into a dialysis patient's body.

2. Description of the Prior Art

The use of dialysis catheters is known in the prior art. More specifically, dialysis catheters heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 5,941,854; U.S. Pat. No. 6,042,566; U.S. Pat. No. 5,843,038; U.S. Pat. No. 6,027,492; U.S. Pat. No. 5,092,853; and U.S. Patent No. Des. 403,064.

While these devices fulfill their respective, particular objectives and requirements, the aforementioned patents do not disclose a new dialysis procedure catheter. The prior art includes syringes and needles being used to withdraw blood and other bodily fluids from patients.

SUMMARY OF THE INVENTION

The general purpose of the present invention, which will be described subsequently in greater detail, is to provide a new dialysis procedure catheter which has many of the advantages of the dialysis catheters mentioned heretofore and many novel features that result in a new dialysis procedure catheter which is not anticipated, rendered obvious, suggested, or even implied by any of the prior art dialysis catheters, either alone or in any combination thereof. The present invention includes a tubular member having a bore being disposed therethrough, and also having an enlarged main portion and a branch portion, and further having needle; and also includes a plug assembly including a plug member being removably disposed in the bore of the needle; and further includes a handle being attached to the enlarged main portion of the tubular member; and also includes a hose having a first end being attached to the branch portion; and further includes a hose clamp for crimping the hose; and also includes a hose connector being attached to a second end of the hose for connecting to a dialysis machine. None of the prior art includes the combination of the elements of the present invention.

There has thus been outlined, rather broadly, the more important features of the dialysis procedure catheter in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

It is an object of the present invention to provide a new dialysis procedure catheter which has many of the advantages of the dialysis catheters mentioned heretofore and many novel features that result in a new dialysis procedure catheter which is not anticipated, rendered obvious, suggested, or even implied by any of the prior art dialysis catheters, either alone or in any combination thereof.

Still another object of the present invention is to provide a new dialysis procedure catheter for accurately and facilitating insertion of a needle into a dialysis patient's body.

Still yet another object of the present invention is to provide a new dialysis procedure catheter that is easy and convenient to use.

Even still another object of the present invention is to provide a new dialysis procedure catheter that eliminates the task of making multiple pricks into a dialysis patient's body.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
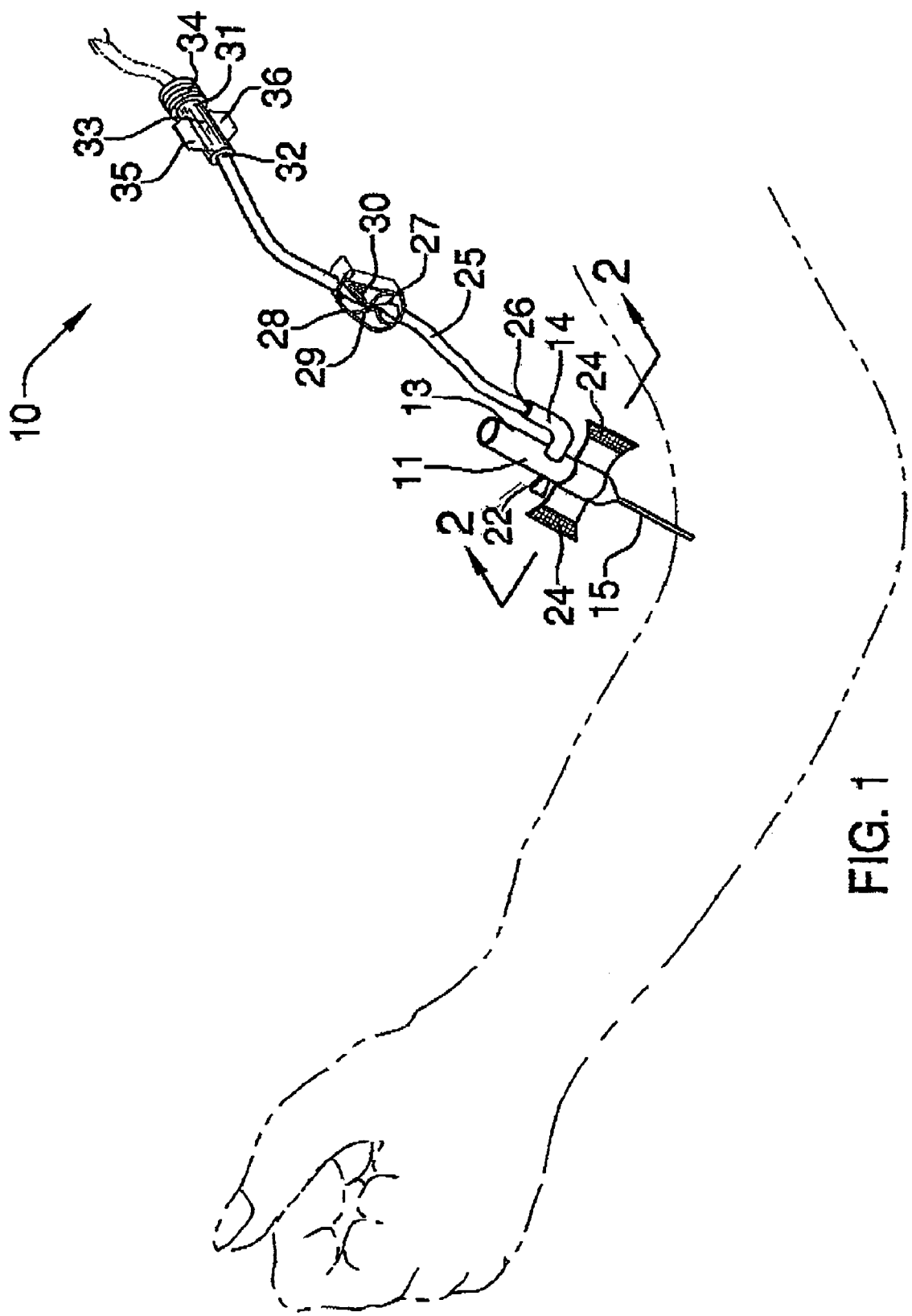
FIG. 1 is a perspective view of a new dialysis procedure catheter according to the present invention and shown in use.
Figure 2:
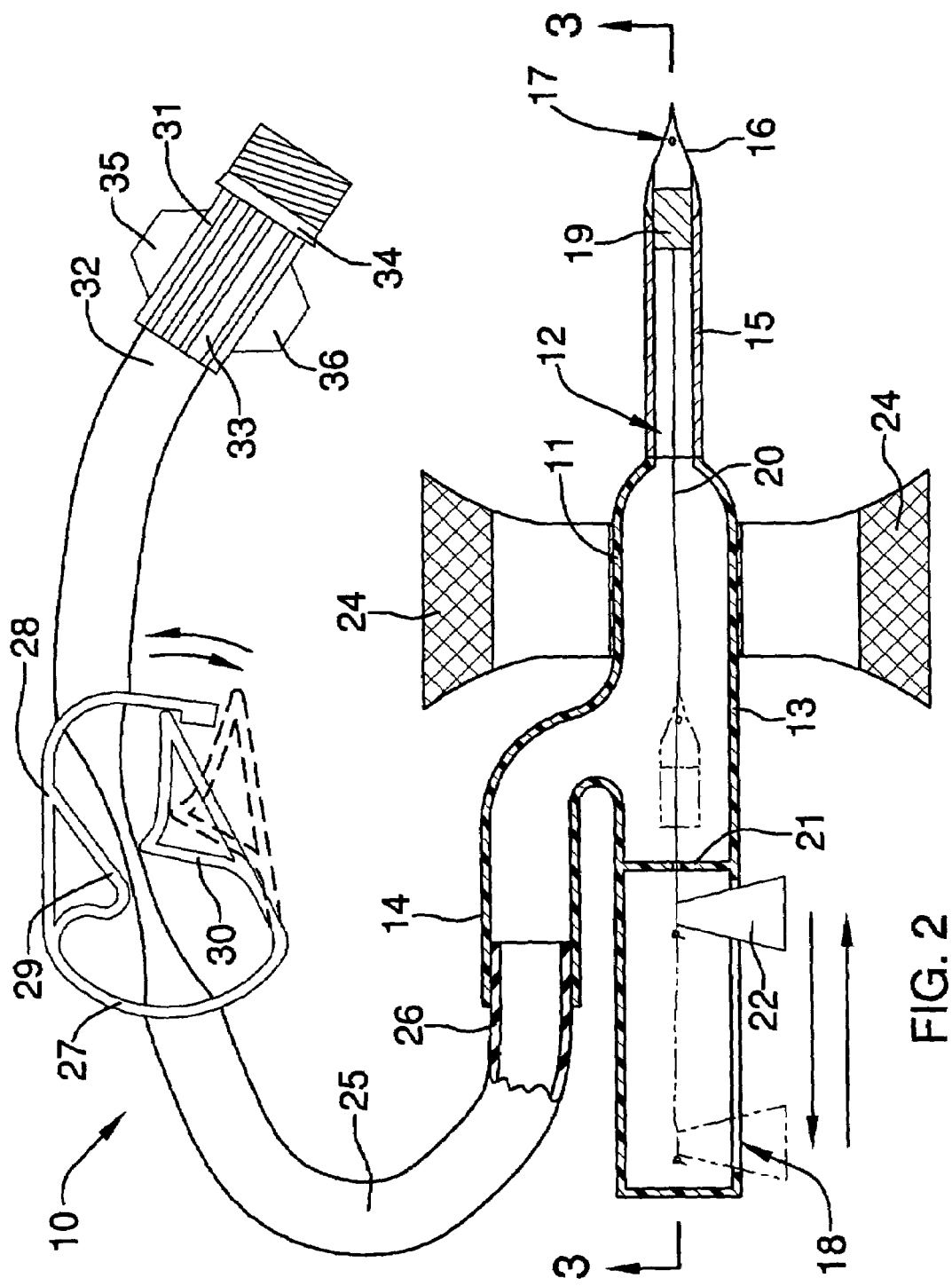
FIG. 2 is a cross-sectional view of the present invention.
Figure 3:
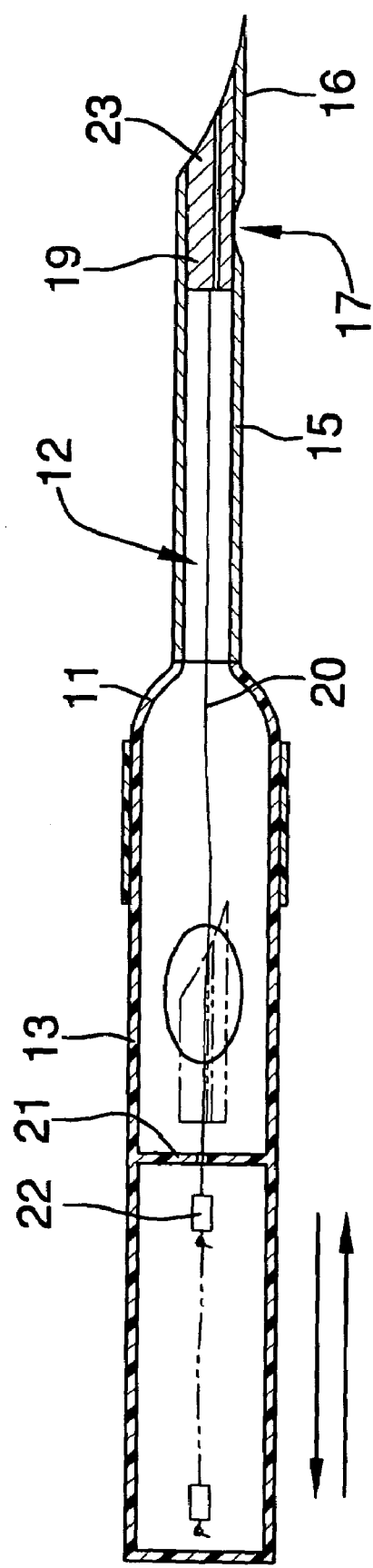
FIG. 3 is another cross-sectional view of the present invention.

With reference now to the drawings, and in particular to FIGS. 1 through 3 thereof, a new dialysis procedure catheter embodying the principles and concepts of the present invention and generally designated by the reference numeral 10 will be described.

As best illustrated in FIGS. 1 through 3, the dialysis procedure catheter 10 generally comprises a tubular member 11 having a bore 12 being disposed therethrough, and also having an enlarged main portion 13 and a branch portion 14, and further having a needle 15. The needle 15 is conventionally connected to the enlarged main portion 13, and has a tapered end 16 for penetrating through a user's skin and vessels, and further has a non-vacuum aperture 17 being disposed through a wall of the needle 15 near the tapered end 16. The enlarged main portion 13 of the tubular member 11 has a longitudinal slot 18 being disposed through a side wall thereof.

A plug assembly includes a plug member 19 being removably disposed in the bore 12 of the needle 15. The plug assembly also includes a wire 20 being conventionally attached to the plug member 19 for the movement thereof, and further includes a flexible diaphragm 21 being securely and conventionally disposed in the bore 12 of the enlarged main portion 13 of the tubular member 11, and also includes a handle member 22 being conventionally attached to an end of the wire 20. The wire 20 is movably disposed through a hole centrally-disposed through the flexible diaphragm 21. The handle member 22 is movably disposed through the longitudinal slot 18 of the enlarged main portion 13 of the tubular member 11. The plug member 19 has a taper end portion 23 which is removably seated in the bore 12 at the tapered end 16 of the needle for closing an opening into the needle 15.

A handle 24 is conventionally attached to the enlarged main portion 13 of the tubular member 11. The handle 24 includes wing shaped members being conventionally attached to an exterior of the enlarged main portion 13 of the tubular member 11 and extend outwardly in opposite directions from one another to facilitate the insertion of the needle 15 into a user's arm. A hose 25 has a first end 26 being conventionally attached to the branch portion 14.

A hose clamp 27 for crimping the hose 25 includes an open-ended ring 28, and also includes triangular-shaped hose pinchers 29,30 being opposedly and conventionally disposed on an inner side of the open-end ring 28 for crimping the hose 25.

A hose connector 31 is conventionally attached to a second end 32 of the hose 25 for connecting to a dialysis machine. The hose connector 31 includes a tubular body 33 having an enlarged end portion 34, and also includes fin-shaped handles 35,36 being opposedly and conventionally attached to the tubular body 33 with the enlarged end portion 34 being externally threaded.

In use, the user inserts the tapered end 16 of the needle 15 into the vein of the patient, and the user pulls back the plug member 19 using the wire 20 to unplug the bore 12 through the tubular member 11 so that the patient's body fluids can be passed through the bore 12 of the tubular member including the branch portion 14. Once finished, the plug member 19 can be seated back into the bore 12 through the needle 15.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the dialysis procedure catheter. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. A dialysis procedure catheter comprising:
   a tubular member having a bore being disposed therethrough, and also having an enlarged main portion, a branch portion, and a needle, said needle being connected to said enlarged main portion, and having a tapered end for penetrating through a user's skin and vessels, and further having a non-vacuum aperture being disposed through a wall of said needle near said tapered end, said enlarged main portion of said tubular member having a longitudinal slot being disposed through a side wall thereof;
   a plug assembly including a plug member being removably disposed in said bore of said needle, said plug assembly also including a wire being attached to said plug member for the movement thereof, and further including a flexible diaphragm being securely disposed in said bore of said enlarged main portion of said tubular member, and also including a handle member being attached to an end of said wire, said wire being movably disposed through a hole centrally-disposed through said diaphragm, said handle member being movably disposed through said longitudinal slot of said enlarged main portion of said tubular member;
   a handle being attached to said enlarged main portion of said tubular member;
   a hose having a first end being attached to said branch portion;
   a hose clamp for crimping said hose; and
   a hose connector being attached to a second end of said hose for connecting to a dialysis machine.

2. The dialysis procedure catheter as described in claim 1, wherein said plug member has a tapered end portion which is removably seated in said bore at said tapered end of said needle for closing an opening into said needle.

3. The dialysis procedure catheter as described in claim 2, wherein said handle includes wing shaped members being attached to an exterior of said enlarged main portion of said tubular member and extending outwardly in opposite directions from one another to facilitate the insertion of said needle into a user's arm.

4. The dialysis procedure catheter as described in claim 3, wherein said hose clamp includes an open ended ring, and also includes triangular-shaped hose pinchers being opposedly disposed on an inner side of said ring for crimping said hose.

5. The dialysis procedure catheter as described in claim 4, wherein said hose connector includes a tubular body having an enlarged end portion, and also includes fin-shaped handles being opposedly attached to said tubular body, said enlarge end portion being externally threaded.

* * * * *